(12) United States Patent
Hodges et al.

(10) Patent No.: US 7,022,217 B2
(45) Date of Patent: *Apr. 4, 2006

(54) ELECTROCHEMICAL METHOD FOR MEASURING CHEMICAL REACTION RATES

(75) Inventors: Alastair Hodges, San Diego, CA (US); Ron Chatelier, San Diego, CA (US)

(73) Assignee: LifeScan, Inc., Milpitas, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 10/196,064

(22) Filed: Jul. 15, 2002

(65) Prior Publication Data

US 2002/0175087 A1 Nov. 28, 2002

Related U.S. Application Data

(63) Continuation of application No. 09/616,556, filed on Jul. 14, 2000, now Pat. No. 6,444,115.

(51) Int. Cl.
*G01N 27/327* (2006.01)
*G01N 27/49* (2006.01)

(52) U.S. Cl. ............................... 205/777.5; 205/793.5

(58) Field of Classification Search ............ 205/777.5, 205/778, 793.5, 792; 204/403.01, 403.1, 204/403.11, 403.14
See application file for complete search history.

(56) References Cited

U.S. PATENT DOCUMENTS

| | | | |
|---|---|---|---|
| 4,053,381 A | 10/1977 | Hamblen et al. | |
| 4,076,596 A | 2/1978 | Connery et al. | |
| 4,224,125 A | 9/1980 | Nakamura et al. | |
| 4,301,412 A | 11/1981 | Hill et al. | |
| 4,301,414 A | 11/1981 | Hill et al. | |
| 4,303,887 A | 12/1981 | Hill et al. | |
| 4,319,969 A | 3/1982 | Oda et al. | |
| 4,374,013 A | 2/1983 | Enfors | |
| 4,404,066 A | 9/1983 | Johnson | |
| 4,431,004 A | 2/1984 | Bessman et al. | |
| 4,431,507 A | 2/1984 | Nankai et al. | |
| 4,508,613 A | 4/1985 | Busta et al. | |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,552,840 A | 11/1985 | Riffer | |
| 4,654,197 A | 3/1987 | Lilja et al. | |
| 4,711,245 A | 12/1987 | Higgins et al. | |
| 4,897,173 A | 1/1990 | Nankai et al. | |
| 4,900,424 A | 2/1990 | Birth et al. | |

(Continued)

FOREIGN PATENT DOCUMENTS

AU   A-31042/93   7/1993

(Continued)

OTHER PUBLICATIONS

Abstract for JP 6310746 A; To: Miyahara et al.

(Continued)

*Primary Examiner*—Alex Noguerola
(74) *Attorney, Agent, or Firm*—Nutter McClennen & Fish LLP

(57) ABSTRACT

The present invention relates to the measurement of the progress of a chemical reaction that generates an electroactive reaction product that is subsequently detected at an electrode amperometrically or coulometrically. The method is useful in applications where it is desirable to follow the progress of a chemical reaction, particularly in sensor applications where the progress of the reaction of an analyte can be useful in determining the analyte concentration.

32 Claims, 3 Drawing Sheets

U.S. PATENT DOCUMENTS

| | | |
|---|---|---|
| 4,919,770 A | 4/1990 | Preidel et al. |
| 4,963,815 A | 10/1990 | Hafeman |
| 4,988,429 A | 1/1991 | Matthiessen |
| 5,059,908 A | 10/1991 | Mina |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,156,972 A | 10/1992 | Issachar |
| 5,192,415 A | 3/1993 | Yoshioka et al. |
| 5,229,282 A | 7/1993 | Yoshioka et al. |
| 5,312,590 A | 5/1994 | Gunasingham |
| 5,314,605 A | 5/1994 | Matthiessen |
| 5,320,732 A | 6/1994 | Nankai et al. |
| 5,382,346 A | 1/1995 | Uenoyama et al. |
| 5,384,028 A | 1/1995 | Ito |
| 5,385,846 A | 1/1995 | Kuhn et al. |
| 5,393,399 A | 2/1995 | Van den Berg et al. |
| 5,413,690 A | 5/1995 | Kost et al. |
| 5,437,999 A | 8/1995 | Diebold et al. |
| 5,496,453 A * | 3/1996 | Uenoyama et al. ...... 205/777.5 |
| 5,508,171 A | 4/1996 | Walling et al. |
| 5,509,410 A | 4/1996 | Hill et al. |
| 5,518,590 A | 5/1996 | Fang |
| 5,567,302 A | 10/1996 | Song et al. |
| 5,611,908 A | 3/1997 | Matthissen et al. |
| 5,620,579 A | 4/1997 | Genshaw et al. |
| 5,628,890 A | 5/1997 | Carter et al. |
| 5,645,709 A | 7/1997 | Birch et al. |
| 5,651,869 A | 7/1997 | Yoshioka et al. |
| 5,863,400 A | 1/1999 | Drummond et al. |
| 5,942,102 A | 8/1999 | Hodges et al. |
| 5,997,817 A | 12/1999 | Crismore et al. |
| 6,117,289 A | 9/2000 | Yamamoto et al. |
| 6,270,637 B1 | 8/2001 | Crismore et al. |
| 6,413,395 B1 * | 7/2002 | Bhullar et al. ......... 204/403.01 |

FOREIGN PATENT DOCUMENTS

| | | |
|---|---|---|
| AU | A-54873/94 | 8/1994 |
| EP | 0 251 915 A2 | 1/1988 |
| EP | 0 255 291 A2 | 2/1988 |
| EP | 0 278 647 A2 | 8/1988 |
| EP | 0 351 516 A2 | 1/1990 |
| EP | 0 418 404 A2 | 3/1991 |
| EP | 0 741 186 A2 | 11/1996 |
| EP | 0 764 469 A2 | 3/1997 |
| EP | 0 964 059 A2 | 12/1999 |
| GB | 2 201 248 A | 8/1988 |
| WO | WO 89/08713 | 9/1989 |
| WO | WO 95/16198 | 6/1995 |
| WO | WO 95/21934 | 8/1995 |
| WO | WO 95/28634 | 10/1995 |
| WO | WO 97/00441 | 1/1997 |
| WO | WO 97/18464 | 5/1997 |
| WO | WO 97/18465 | 5/1997 |
| WO | WO 98/11426 | 3/1998 |
| WO | WO 98/43073 | 10/1998 |
| WO | WO 98/43074 | 10/1998 |
| WO | WO 99/46585 | 9/1999 |

OTHER PUBLICATIONS

CAPLUS Abstract of Uchiyama et al. "Measurement of homogeneous reaction rate by concentration-step, controlled potential electrolysis," *J Electroanal. Chem. Interfacial Elctrochem.*, 91(3):301-308, 1978.

CAPLUS Abstract of Trojanek et al. "Data processing in reaction rate measurements," *Collect. Chzech. Chem Commun.*, 38(9):2572-2580, 1973.

* cited by examiner

ELECTROCHEMICAL METHOD FOR MEASURING CHEMICAL REACTION RATES

RELATED APPLICATION

This application is a continuation of application Ser. No. 09/616,556 now U.S. Pat. No. 6,444,115, filed Jul. 14, 2000.

BACKGROUND FIELD OF THE INVENTION

1. Field of the Invention

The present invention relates to the measurement of the progress of a chemical reaction that generates an electroactive reaction product that is subsequently detected at an electrode amperometrically or coulometrically. The method is useful in applications where it is desirable to follow the progress of a chemical reaction, particularly in sensor applications where the progress of the reaction of an analyte can be useful in determining the analyte concentration.

2. Description of the Related Art

In amperometric electrochemistry the current flowing at the electrode can be used as a measure of the concentration of electroactive species being reacted electrochemically at the working electrode. In coulometry the current flowing at the electrode is integrated over time to give a total amount of charge passed which yields a measure of the amount of electroactive material reacted at the working electrode. The current flowing (or charge passed at any time) at the electrode is dependent upon the rate of transfer of the electroactive species to the working electrode. When a significant concentration of electroactive species is situated close to the electrode and an electrical potential is applied to the electrode sufficient to electrochemically react the electroactive species at the electrode/solution interface, initially a higher current will flow which will diminish with time. For an isolated electrode, where the potential applied to the electrode is sufficient to react the electroactive species effectively instantaneously upon arriving at the electrode and the transfer of electroactive species to the electrode is controlled by diffusion, the current will follow a curve known in the art as the Cottrell Equation. According to this equation the current varies inversely with the square root of time. This yields a current which decays with time as the electroactive species that reacts at the electrode becomes depleted close to the electrode and so electroactive species has to travel from further and further away to reach the electrode as time progresses.

If in addition to the electrochemical reaction of the electroactive species at the electrode the electroactive species is being generated close to the working electrode by a chemical reaction, the form of the current flowing at the electrode becomes complex. The electrode reaction tends to decrease the concentration of electroactive species close to the working electrode whereas the chemical reaction tends to increase the concentration of the electroactive species in this region. The time dependent behavior of these two processes therefore mix and it is difficult to measure the chemical reaction kinetics from the current flowing (or charge passed) at the electrode.

For this reason, in the published literature, the rates of chemical reactions are not generally measured electrochemically except in specialized applications using specialized equipment. An example of such equipment is known in the art as a rotating ring/disc electrode. This apparatus is only applicable to relatively fast reaction kinetics and requires that the electrode be rotated at a known controlled rate with well characterized liquid hydrodynamics.

SUMMARY OF THE INVENTION

The method of the present invention allows for the extraction of chemical reaction rate information using a simple electrochemical method and apparatus.

In a first aspect of the present invention, a method is provided for measuring a rate of a chemical reaction between a component of a liquid sample and a reagent, the reaction producing an electroactive species, including providing an electrochemical cell having a working electrode, a counter electrode, and at least one wall; substantially immobilizing the reagent in the electrochemical cell at a site at a minimum distance from the working electrode, wherein the distance is such that transfer of the electroactive species from the site to the working electrode is diffusion controlled; placing the liquid sample in the electrochemical cell such that the liquid sample is in contact with the reagent, the working electrode, and the counter electrode; reacting the component with the reagent to produce the electroactive species; applying a potential between the working electrode and the counter electrode, wherein the potential is sufficient to electrochemically react the electroactive species at the working electrode; and measuring the current produced by the electrochemical reaction at the working electrode to obtain a measure of the rate of the chemical reaction.

In one aspect of this embodiment, the working electrode and the counter electrode are sufficiently spaced such that a product of an electrochemical reaction occurring at the counter electrode does not reach the working electrode while the current is measured. The working electrode and the counter electrode may be spaced apart at a distance greater than about 500 microns; between about 500 microns and about 5 mm; or between about 1 mm and about 2 mm. The working electrode and the counter electrode may be situated on the same plane.

In another aspect of this embodiment, the site and the working electrode are separated by a minimum distance ranging from about 10 microns to about 5 millimeters; from about 50 microns to about 500 microns; or from about 100 microns to about 200 microns.

In another aspect of this embodiment, the counter electrode is capable of functioning as a combined counter/reference electrode. The electrochemical cell may further include a reference electrode.

In another aspect of this embodiment, the working electrode functions as an anode, and may include platinum, palladium, carbon, carbon in combination with one or more inert binders, iridium, indium oxide, tin oxide, indium in combination with tin oxide, and mixtures thereof.

In another aspect of this embodiment, the working electrode functions as an cathode and may include platinum, palladium, carbon, carbon in combination with one or more inert binders, iridium, indium oxide, tin oxide, indium in combination with tin oxide, steel, stainless steel, copper, nickel, silver, chromium, and mixtures thereof.

In another aspect of this embodiment, the counter electrode includes platinum, palladium, carbon, carbon in combination with inert binders, iridium, indium oxide, tin oxide, indium in combination with tin oxide, steel, stainless steel, copper, nickel, chromium, silver, and mixtures thereof. The counter electrode may also include silver coated with a substantially insoluble silver salt, such as silver chloride, silver bromide, silver iodide, silver ferrocyanide, and silver ferricyanide.

In another aspect of this embodiment, the site is situated on the counter electrode or on the wall. The site and the working electrode may be situated on the same plane or in a plane facing and substantially parallel to the working electrode.

In another aspect of this embodiment, the reagent is contained within a polymeric matrix attached to a surface in the electrochemical cell; is chemically tethered to a surface in the electrochemical cell; is physically tethered to a surface in the electrochemical cell; or is dried onto a surface in the electrochemical cell and exhibits sufficiently low mobility in the liquid sample such that the reagent does not substantially migrate while the current is measured.

In another aspect of this embodiment, the method further includes a redox mediator. The redox mediator may include ferrocinium, osmium complexes with bipyridine, benzophenone, and ferricyanide.

In another aspect of this embodiment, the sample may include whole blood. The component may include glucose. The reagent may include an enzyme such as PQQ dependent glucose dehydrogenase, NAD dependent glucose dehydrogenase, glucose oxidase, lactate dehydrogenase, and alcohol dehydrogenase.

In another aspect of this embodiment, the potential is preferably between +50 and +500 mV, and more preferably about +300 mV.

In a second embodiment of the present invention, a method is provided for measuring a rate of a chemical reaction between glucose and PQQ dependent glucose dehydrogenase in whole blood including providing an electrochemical cell having a working electrode, a counter electrode, at least one wall, a redox mediator including ferricyanide and contained within the electrochemical cell, and a reagent including PQQ dependent glucose dehydrogenase, the reagent being substantially immobilized in the electrochemical cell at a site at a minimum distance from the working electrode; placing the whole blood sample in the electrochemical cell such that the sample is in contact with the reagent, the redox mediator, the working electrode, and the counter electrode; reacting the glucose with the PQQ dependent glucose dehydrogenase to produce reduced PQQ dependent glucose dehydrogenase, the reduced PQQ dependent glucose dehydrogenase in turn reacting with the ferricyanide redox mediator to form ferrocyanide; applying a potential between the working electrode and the counter electrode, wherein the potential is sufficient to electrochemically react the ferrocyanide at the working electrode; and measuring the current produced by the electrochemical reaction of ferrocyanide at the working electrode, wherein the measurement is indicative of the rate of the chemical reaction between glucose and PQQ dependent glucose dehydrogenase.

DETAILED DESCRIPTION OF THE PREFERRED EMBODIMENT

Figure 1:
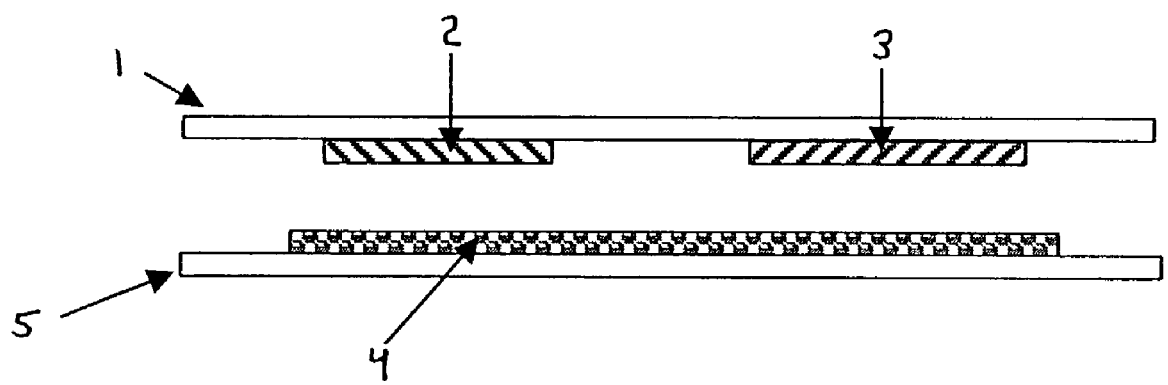
FIG. 1 depicts an electrochemical cell wherein the reagent is situated on a wall of the cell facing the working electrode.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

According to the present invention, information relating to the rate of a chemical reaction that yields at least one electroactive product can be obtained using an electrochemical cell by ensuring that the chemical reaction is localized at a site remote from the electrode used to electrochemically react the electroactive product(s).

Methods and devices for obtaining electrochemical measurements of fluid samples are discussed further in copending U.S. patent application Ser. No. 09/616,433, filed on Jul. 14,2000, entitled "IMMUNOSENSOR," copending U.S. patent application Ser. No. 09/616,512, filed on Jul. 14, 2000, entitled "HEMOGLOBIN SENSOR," and copending U.S. patent application Ser. No. 09/615,691, filed on Jul. 14, 2000, entitled "ANTIOXIDANT SENSOR," each of which is incorporated herein by reference in its entirety.

The site of the chemical reaction needs to be sufficiently removed from the electrode such that the mass transfer of the electroactive species from the chemical reaction site to the electrode effectively controls the current flowing at the electrode at any time. This arrangement ensures a substantially linear electroactive species concentration gradient between the chemical reaction site and the electrode. The concentration of the electroactive species is maintained at effectively zero at the electrode by the electrochemical reaction taking place there. The time course of the magnitude of this concentration gradient will therefore be substantially determined only by the time course of the concentration of the electroactive specie(s) at the chemical reaction site and the diffusion coefficient(s) of the electroactive reaction product(s) in the liquid medium. Since the current flowing at the electrode is proportional to the concentration gradient of the electroactive specie(s) at the electrode, the time course of this current will reflect the time course of the chemical reaction occurring at the remote site. This allows the current measured at the electrode (or charge passed if the current is integrated) to be a used as a convenient measure of the rate and extent of the chemical reaction taking place.

An example of a suitable method for ensuring that the chemical reaction is remote from the working electrode is to immobilize one or more of the reaction components on a solid surface remote from the electrode. The reaction component(s) can be immobilized by incorporating them in a polymeric matrix that is dried on or otherwise attached to the solid surface. The reaction component(s) can also be tethered directly to the solid surface either by chemical or physical bonding. Alternatively one or more of the reaction components can simply be dried onto the solid surface without special immobilization means. In this situation one or more of the reaction components needs to be sufficiently low in mobility, in the liquid matrix filling the electrochemical cell, that it does not migrate substantially from the position where it was dried during the time period that the electrochemical current can be usefully monitored to perform the required measurement. In this context substantial migration means that the slowest moving component required for the chemical reaction approaches closely enough to the working electrode that Cottrell type depletion kinetics begin to effect the time course of the current flowing at the electrode.

The range of separation distance between the chemical reaction site and the working electrode in the present invention is desirably less than about 1 cm, preferably less than 5 mm, more preferably between 5, 10, 50, 100, 200, 500 microns and 5 mm, more preferably between 5, 10, 50, 100, 200 and 500 microns, and most preferably between 5, 10, 50, 100 and 200 microns.

As well as the working electrode, at least a counter electrode in contact with the liquid sample needs to be provided to complete the electrochemical circuit. Optionally the counter electrode can function as a combined counter/reference electrode or a separate reference electrode can be provided. In a preferred embodiment, the working electrode and counter electrode are desirably spaced apart at a distance greater than about 300 microns, preferably at a distance greater than about 500 microns, more preferably at a distance between about 500 microns and 10 mm, more preferably at a distance between about 500 microns and 1, 2, 5 mm, and most preferably between 1 mm and 2, 5, 10 mm.

The working electrode needs to be constructed of materials that do not react chemically with any component with which it will come into contact during use to an extent that interferes with the current response of the electrode. If the working electrode is to be used as an anode then examples of suitable materials are platinum, palladium, carbon, carbon in combination with inert binders, iridium, indium oxide, tin oxide, mixtures of indium and tin oxide. If the working electrode is to be used as a cathode then in addition to the material listed above other suitable materials are steel, stainless steel, copper, nickel, silver and chromium.

Examples of materials suitable for the counter electrode are platinum, palladium, carbon, carbon in combination with inert binders, iridium, indium oxide, tin oxide, mixture of indium and tin oxide, steel, stainless steel, copper, nickel, chromium, silver and silver coated with a substantially insoluble silver salt such as silver chloride, silver bromide, silver iodide, silver ferrocyanide, silver ferricyanide.

The site of the chemical reaction can be localized on a bare wall or on the counter electrode, remote from the working electrode. The site of the chemical reaction can be on the same plane as the working electrode or more preferably in a plane facing and substantially parallel to the working electrode.

FIG. 1 depicts an apparatus suitable for use with one embodiment of the current invention. In FIG. 1, a working electrode 2 and a counter electrode 3 are disposed on an electrically insulating substrate 1. On a second substrate 5 is disposed a layer of chemical reactants 4, where at least one of the reactants is substantially immobilized on the substrate 5. In use, the space between walls 1 and 5 is filled with a liquid containing a substance which is capable of reacting with the reagents 4 to produce at least one electroactive species. The products of the chemical reaction diffuse towards the working electrode 2 where the electroactive specie(s) are electrochemically reacted to produce a current. The magnitude of the current or the charge passed at a particular time, or the time course of the current or charge passed can then be used to obtain a measure of the rate or extent of the chemical reaction occurring at the reactant layer 4.

Figure 2:
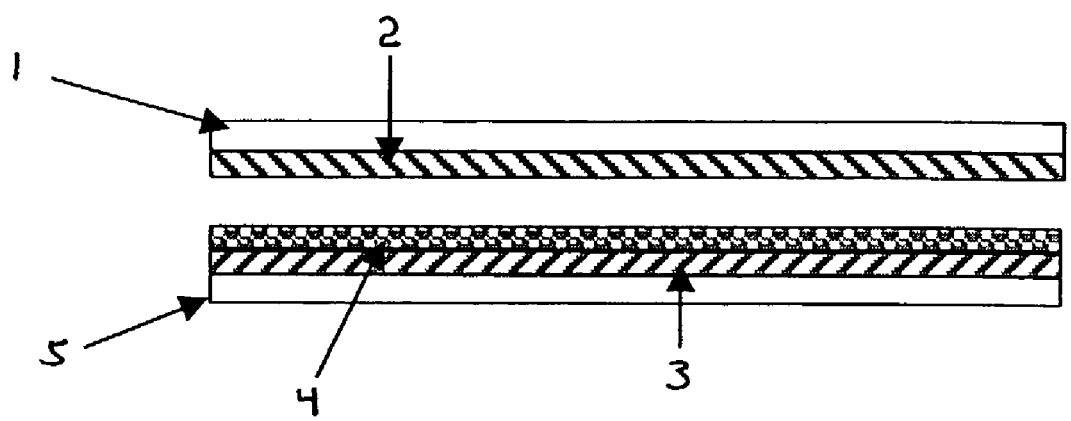
FIG. 2 depicts an electrochemical cell wherein the reagent is situated on the counter electrode.

FIG. 2 depicts another embodiment of the current invention. The numbering of the components in FIG. 2 correspond to the components in FIG. 1. In FIG. 2 the reactants 4 are disposed on the counter electrode 3 which is disposed on an electrically resistive substrate 5. In this embodiment the materials of construction of the counter electrode 3 must be inert to reaction with any of the components of the reactants 4 disposed on the electrode 3.

An example of a chemistry and reaction that is suitable for use with the current invention is measuring glucose in whole blood using the enzyme PQQ dependent glucose dehydrogenase (GDHpqq) and a redox mediator. In this reaction glucose in the blood reacts with GDHpqq to form gluconic acid. In the process, the PQQ in the enzyme is reduced. A mediator, such as potassium ferricyanide, then oxidizes the PQQ in the enzyme and forms ferrocyanide. The enzyme in the oxidized form can then react with further glucose. The net effect of this reaction is to produce two ferrocyanide molecules for each glucose molecule reacted. Ferrocyanide is an electroactive species, and so can be oxidized at an electrode to produce a current. Other suitable enzymes for this reaction are glucose oxidase (GOD) or NAD dependent glucose dehydrogenase. For other reactions, lactate dehydrogenase and alcohol dehydrogenase may be used. Other suitable redox mediators include ferrocinium, osmium complexes with bipyridine, and benzophenone.

The reaction of glucose in whole blood with the enzyme can be slow, taking up to a few minutes to go to completion. Also, the higher the haematocrit of the blood sample, the slower the reaction. The haematocrit of the blood is the volume fraction of red cells in the whole blood sample. In this example, an electrochemical cell according to FIG. 2 was constructed. A solution containing 50 mg/ml GDHpqq, 0.9 M potassium ferricyanide and 50 mM buffer at pH 6.5 was deposited on the counter electrode and the water removed to leave a dried reactant layer. In this layer the GDHpqq is large enough to be effectively immobilized on the counter electrode, whereas the ferricyanide can mix more evenly throughout the liquid in the electrochemical cell. The blood sample was introduced into the cell and a potential of +300 mV immediately applied between the working electrode and the counter electrode. Although a potential of +300 mV is most preferred for oxidizing ferrocyanide, the potential is desirably between +40 mV and +600 mV, preferably between +50 mV and +500 mV, and more preferably between +200 mV and +400 mV. In the cell, the working electrode consisted of a layer of gold sputtered onto a polyester substrate and the counter electrode consisted of a layer of palladium sputtered onto a polyester substrate.

Figure 3:
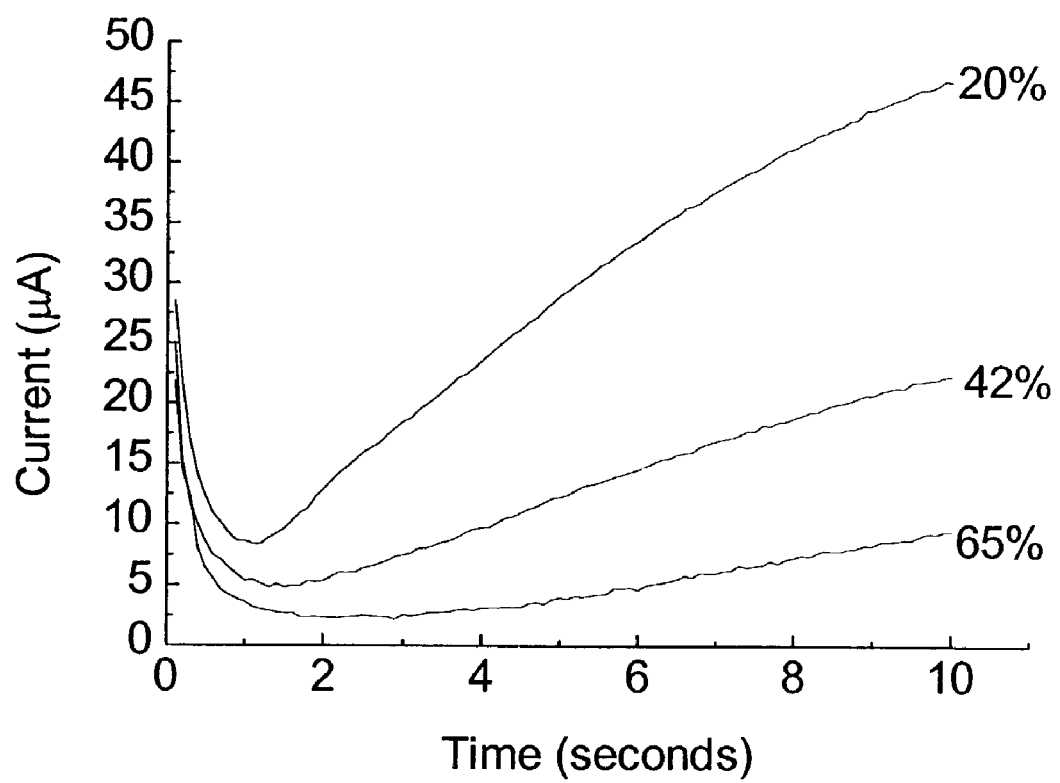
FIG. 3 shows current as a function of time for three whole blood samples for a reaction system including glucose, PQQ dependent glucose dehydrogenase and potassium ferrocyanide redox mediator. The three blood samples contain haematocrit levels of 20%, 42%, and 65%, respectively, where the haematocrit is the volume percent of red blood cells in the sample.

The current traces recorded for blood samples of different haematocrits, showing a faster rate of reaction in lower haematocrit blood, are given in FIG. 3. The number at the end of each line is the percent haematocrit of the blood sample used, i.e., 20%, 42%, and 65%, respectively. The glucose level in each blood sample is approximately the same, namely 5.4 mM for the 65% haematocrit sample, 5.5 mM for the 42% haematocrit sample, and 6.0 mM for the 20% haematocrit sample.

The current shown in FIG. 3 can be approximately given by the equation:

$$i = -FADC/L$$

where i is the current, F is Faraday's constant (96486.7 C/mole), A is the electrode area, D is the diffusion coefficient of the ferrocyanide in the sample, C is the concentration of ferrocyanide at the reaction site and L is the distance between the reaction site and the electrode. The reaction rate, given by the rate of change of C with time is therefore given by:

$$dC/dt = -(L/FAD)di/dt.$$

For the reactions depicted in FIG. 3, between 6 and 8 seconds for the 20%, 42% and 65% haematocrit samples, the average di/dt was 3.82, 2.14 and 1.32 microamps/second, respectively. The diffusion coefficients of ferrocyanide for these samples were $2.0 \times 10^{-6}$, $1.7 \times 10^{-6}$ and $1.4 \times 10^{-6}$ cm$^2$/sec for 20%, 42%, and 65% haematocrit samples, respectively. The electrode area was 0.1238 cm$^2$ and L was 125 microns. These values yield reaction rates of 2.0, 1.3, and 0.99 mM/second for the 20%, 42% and 65% haematocrit samples, respectively.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for measuring a rate of a chemical reaction between a component of a liquid sample and a reagent, the reaction producing an electroactive species, comprising:
   providing an electrochemical cell having a working electrode, a counter electrode, and at least one wall, wherein the working electrode and the counter electrode are positioned on substantially the same plane;
   substantially immobilizing the reagent in the electrochemical cell at a site at a minimum distance from the working electrode, wherein the distance is such that transfer of the electroactive species from the site to the working electrode is diffusion controlled;
   placing the liquid sample in the electrochemical cell such that the liquid sample is in contact with the reagent, the working electrode, and the counter electrode;
   reacting the component with the reagent to produce the electroactive species;
   applying a potential between the working electrode and the counter electrode, wherein the potential is sufficient to electrochemically react the electroactive species at the working electrode; and
   measuring the current produced by the electrochemical reaction at the working electrode to obtain a measure of the rate of the chemical reaction.

2. The method according to claim 1, wherein the working electrode and the counter electrode are sufficiently spaced such that a product of an electrochemical reaction occurring at the counter electrode does not reach the working electrode while the current is measured.

3. The method according to claim 2, wherein the working electrode and the counter electrode are spaced apart at a distance greater than about 500 microns.

4. The method according to claim 3, wherein the distance is between about 500 microns and about 5 mm.

5. The method according to claim 4, wherein the distance is between about 1 mm and about 2 mm.

6. The method according to claim 1, wherein the site and the working electrode are separated by a minimum distance ranging from about 10 microns to about 5 millimeters.

7. The method according to claim 6, wherein the minimum distance ranges from about 50 microns to about 500 microns.

8. The method according to claim 7, wherein the minimum distance ranges from about 100 microns to about 200 microns.

9. The method of claim 1, wherein the counter electrode is capable of functioning as a combined counter/reference electrode.

10. The method of claim 1, wherein the electrochemical cell further comprises a reference electrode.

11. The method according to claim 1, wherein the working electrode functions as an anode.

12. The method according to claim 11, wherein the working electrode comprises a material selected from the group consisting of platinum, palladium, carbon, carbon in combination with one or more inert binders, iridium, indium oxide, tin oxide, indium in combination with tin oxide, and mixtures thereof.

13. The method according to claim 1, wherein the working electrode functions as a cathode.

14. The method according to claim 13, wherein the working electrode comprises a material selected from the group consisting of platinum, palladium, carbon, carbon in combination with one or more inert binders, iridium, indium oxide, tin oxide, indium in combination with tin oxide, steel, stainless steel, copper, nickel, silver, chromium, and mixtures thereof.

15. The method according to claim 1, wherein the counter electrode comprises a material selected from the group consisting of platinum, palladium, carbon, carbon in combination with inert binders, iridium, indium oxide, tin oxide, indium in combination with tin oxide, steel, stainless steel, copper, nickel, chromium, silver, and mixtures thereof.

16. The method according to claim 1, wherein the counter electrode comprises silver coated with a substantially insoluble silver salt.

17. The method according to claim 16, wherein the silver salt is selected from the group consisting of silver chloride, silver bromide, silver iodide, silver ferrocyanide, and silver ferricyanide.

18. The method according to claim 1, wherein the site is situated on the wall.

19. The method according to claim 1, wherein the site is situated in a plane facing and substantially parallel to the working electrode.

20. The method according to claim 1, wherein the reagent is contained within a polymeric matrix attached to a surface in the electrochemical cell.

21. The method according to claim 1, wherein the reagent is chemically tethered to a surface in the electrochemical cell.

22. The method according to claim 1, wherein the reagent is physically tethered to a surface in the electrochemical cell.

23. The method according to claim 1, wherein the reagent is dried onto a surface in the electrochemical cell, the reagent exhibiting sufficiently low mobility in the liquid sample such that the reagent does not substantially migrate while the current is measured.

24. The method according to claim 23, wherein the sample comprises whole blood.

25. The method according to claim 23, wherein the component comprises glucose.

26. The method according to claim 25, wherein the reagent comprises an enzyme selected from the group consisting of PQQ dependent glucose dehydrogenase, NAD dependent glucose dehydrogenase, glucose oxidase, lactate dehydrogenase, and alcohol dehydrogenase.

27. The method according to claim 1, further comprising a redox mediator.

28. The method according to claim 1, wherein the redox mediator is selected from the group consisting ferrocinium, osmium complexes with bipyridine, and benzophenone.

29. The method according to claim 1, wherein the redox mediator comprises ferricyanide.

30. The method according to claim 29, wherein the potential is between about +50 mV and +500 mV.

31. The method according to claim 29, wherein the potential is about +300 mV.

32. A method for measuring a rate of a chemical reaction between glucose and PQQ dependent glucose dehydrogenase in whole blood comprising:

providing an electrochemical cell having a working electrode, a counter electrode, at least one wall, a redox mediator comprising ferricyanide and contained within the electrochemical cell, and a reagent comprising PQQ dependent glucose dehydrogenase, the reagent being substantially immobilized in the electrochemical cell at a site at a minimum distance from the working electrode, wherein the working electrode and the counter electrode are positioned on substantially the same plane;

placing the whole blood sample in the electrochemical cell such that the sample is in contact with the reagent, the redox mediator, the working electrode, and the counter electrode;

reacting the glucose with the PQQ dependent glucose dehydrogenase to produce reduced PQQ dependent glucose dehydrogenase, the reduced PQQ dependent glucose dehydrogenase in turn reacting with the ferricyanide redox mediator to form ferrocyanide; applying a potential between the working electrode and the counter electrode, wherein the potential is sufficient to electrochemically react the ferrocyanide at the working electrode; and measuring the current produced by the electrochemical reaction of ferrocyanide at the working electrode, wherein the measurement is indicative of the rate of the chemical reaction between glucose and PQQ dependent glucose dehydrogenase.

* * * * *